(12) United States Patent
Nissl

(10) Patent No.: US 7,645,297 B2
(45) Date of Patent: Jan. 12, 2010

(54) STENT

(75) Inventor: Thomas Nissl, Garstedt (DE)

(73) Assignee: Qualimed Innovative Medizinprodukte GmbH, Winsen (DE)

( * ) Notice: Subject to any disclaimer, the term of this patent is extended or adjusted under 35 U.S.C. 154(b) by 242 days.

(21) Appl. No.: 10/596,622

(22) PCT Filed: Jan. 11, 2005

(86) PCT No.: PCT/DE2005/000018

§ 371 (c)(1),
(2), (4) Date: Jun. 19, 2006

(87) PCT Pub. No.: WO2005/104990

PCT Pub. Date: Nov. 10, 2005

(65) Prior Publication Data

US 2008/0154353 A1 Jun. 26, 2008

(30) Foreign Application Priority Data

May 3, 2004 (DE) .................. 10 2004 022 044

(51) Int. Cl.
*A61F 2/06* (2006.01)
(52) U.S. Cl. .................. 623/1.15; 623/1.16; 623/1.17
(58) Field of Classification Search ....... 623/1.15–1.22, 623/1.31–1.34; *A61F 2/06*
See application file for complete search history.

(56) References Cited

U.S. PATENT DOCUMENTS

| 5,861,027 | A | 1/1999 | Trapp |
| 5,876,449 | A | 3/1999 | Starck et al. |
| 6,475,236 | B1 | 11/2002 | Roubin et al. |
| 6,602,285 | B1 | 8/2003 | Von Oepen et al. |
| 6,786,922 | B2 * | 9/2004 | Schaeffer ............... 623/1.15 |
| 6,878,162 | B2 * | 4/2005 | Bales et al. ............. 623/1.15 |
| 7,004,968 | B2 | 2/2006 | Lootz et al. |
| 2002/0049487 | A1* | 4/2002 | Lootz et al. ............ 623/1.11 |
| 2005/0222670 | A1* | 10/2005 | Schaeffer ............... 623/1.15 |

FOREIGN PATENT DOCUMENTS

| DE | 295 21 206 U | 10/1996 |
| DE | 297 02 671 U | 5/1997 |
| EP | 1 088 528 A | 4/2001 |
| WO | WO 96/26689 | 9/1996 |
| WO | WO 98/22159 A | 5/1998 |
| WO | WO 99/16387 A | 4/1999 |
| WO | WO 02/24111 A | 3/2002 |
| WO | WO 2004/084769 | 10/2004 |

\* cited by examiner

*Primary Examiner*—Thomas C Barrett
*Assistant Examiner*—Jason-Dennis Stewart
(74) *Attorney, Agent, or Firm*—Henry M. Feiereisen; Ursula B. Day

(57) ABSTRACT

Disclosed is a stent (1) representing a prosthesis for a constricted body vessel. The stent (1) includes a tubular support frame (2) composed of ring segments (3, 4, 5) which are sequentially arranged in axial direction and which are formed by segment struts (5, 6) that are continuously joined to one another in the initial state via transitions (8). Adjacent ring segments (3-5) are coupled to each other using tie bars (9, 10). In order to prevent notch stress in the segment struts (5, 6), the width thereof increases from midsection (16) in the direction of the transitions (8), wherein the segment struts (6, 7) are curved in a wave-like manner.

8 Claims, 3 Drawing Sheets

STENT

BACKGROUND OF THE INVENTION

The invention relates to a stent.

Stents are used to provide permanent or temporary support of body vessels which are closed or narrowed due to stenosis.

The stents have a tubular support frame made of metal, with the support frame having several ring segments. The ring segments are formed of segment struts which are sequentially arranged in an endless manner and joined by transitions. Adjoining ring segments along the longitudinal axis of the stent are coupled by tie bars.

Stents are available in different constructions and designs of the support frame. WO 96/26689, U.S. Pat. No. 5,861,027 A, DE 297 02 671 U1 or DE 295 21 206 U1 are mentioned here as examples.

The stents are inserted using catheter procedures and similar insertion methods into the intravascular region near the stenosis and placed there, whereby the support frame can be widened from the initial state to a supporting state which is increased in diameter. This widening process can occur automatically with so-called self-expanding stents, but can also be initiated by using a suitable tool, for example a balloon catheter. The stents operate in the vessel as a vascular prosthesis for supporting the interior walls of the vessel.

The self-expanding stents include stents made of so-called shape-memory alloys. One exemplary shape-memory alloy is nitinol which is a nickel-titanium alloy. It has two defined phase regions which depend on the temperature. After pretreatment, nitinol is martensitic in the cold state, i.e., plastically deformable without a significant elastic restoring force. Upon heating, the material transforms into an austenitic elastic state. This shape-memory characteristic is used for self-expansion of the stent.

A conventional fabrication method for manufacturing stents includes slitting a thin walled metallic tube according to the desired contour of the support frame and subsequently spreading the tube apart. The tube is slit by laser cutting. The employed tubes typically have an initial diameter of 1.4-1.8 mm and produce stents with a diameter of 5-12 mm. With the conventional designs of the support frame, the employed cutting technique necessitates that the segment struts are cut out with a parallel cutting geometry, and no other options are available. However, this approach produces a high notch stress at the ends of the segment struts and in the region of the transitions, respectively, and thus lead to a high risk of fractures.

SUMMARY OF THE INVENTION

Based on the state of the art, it is therefore an object of the invention to provide a stent which has improved an stress pattern in the segment struts, and in which stress is reduced in the ends of the segment struts and distributed over the length of the segment struts.

According to the invention, a stent has a tubular support frame which can be widened from an initial state to a supporting state. The support frame includes ring segments sequentially arranged along the longitudinal axis of the stent, with the ring segments formed of an endless sequence of segment struts arranged in the circumferential direction of the support frame. Adjoining ring segments are coupled by tie bars. According to a core feature of the invention, the segment struts are curved in a wave-like manner, with the width of the segment struts, as measured perpendicular to the longitudinal axis of the struts, increasing from midsection in direction of the transitions. The width of the segment struts measured in the circumferential direction of the support frame remains constant along the length of the segment struts. Accordingly, the segment struts are narrower in midsection than at their respective ends, as measured in the perpendicular direction, so that stress is distributed over the entire length of a segment strut, and the stress is reduced at the ends as a consequence of the larger cut-out width. This reduces the risk of fracture in the particularly critical regions at the ends of the segment struts and thus significantly increases the service life of a stent.

The support frame has a wave-like design in the absence of straight strut sections in parallel relationship. The segment struts become wider from midsection to their respective ends in accordance with a continuous contour course.

Preferably, the ratio of the wave radius to the width of a segment strut changes from the center toward the ends of the segment strut at a ratio of 10:1 to 15:1.

The stent according to the invention can be easily crimped while having high flexibility. In the supporting state, it is characterized by high stability and high radial stiffness with improved restenosis frequency.

The stent is made of metal. All deformable, medically possible metals and metal alloys can be used, e.g. stainless steel, cobalt alloys (phynox), pure iron, or in particular nickel-titanium alloys.

The support frame is produced by slitting a preferably metallic tube with a laser beam. The laser beam follows the predetermined cutting contour with a focus setting providing a beam width of, for example, 20-30 µm. The geometry, i.e., the width, of the segment struts is changed by selecting a suitable radius and changing the radius in the longitudinal direction of the segment strut toward the transition.

It is of particular advantage that the contour or configuration of the support frame can be produced simply by slitting the starting tube, so that the geometric shape need not be produced from a solid piece.

For practical applications, the stent according to the invention may also be produced from a plastic material. Planned is, in particular, the use of a bio-resorbable plastic. The stent can then preferably be made by injection molding.

The stress distribution can be optimized by shaping the segment struts and the support frame, respectively, in accordance with the invention.

According to another feature of the present invention, first and second tie bars are provided. Each tie bar has an arm extending in the circumferential direction of the support frame, with both sides of the arm being connected via axial sections to a transition. This configuration of the tie bars contributes to the stability of a stent in the longitudinal direction.

The arm in the tie bars compensates for a decrease in the length of the support frame, which is theoretically a result of the widening process and the transition of the segment struts into a widened, stretched shape.

Advantageously, the axial sections of the first tie bars are also curved in a wave-like manner. The width of the axial sections, as measured perpendicular to the longitudinal axis of the axial sections, increases from the arms toward the transitions.

Particularly advantageous is a ratio of the curvature or wave radius of the axial sections to the width of the axial sections, which changes from the arms to the ends in a range between 12:1 and 20:1.

According to another feature of the present invention, the arms of the tie bars extending in the circumferential direction are arranged in the space between two axially spaced apart adjacent ring segments.

According to another feature of the present invention, each of the first tie bars extends from the bottom of two interconnected segment struts of a ring segment to a bottom of two interconnected segment struts of an adjacent ring segment.

Conversely, each of the second tie bars extends from the tip of two interconnected segment struts of a ring segment to the tip of two interconnected segment struts of the adjacent ring segment.

According to another feature of the present invention, the first tie bars of a ring segment and the second tie bars of the adjacent ring segment are disposed in offset relationship in the circumferential direction.

According to another feature of the present invention, a measure which improves the application of the inventive stent provides that the end face of each third transition includes a widened head end disposed on the terminal ring segments, as viewed along the longitudinal stent axis, with the widened head end protruding axially beyond the adjacent transitions.

The head ends, which are advantageously rounded, provide a gentle contact between the end faces of the stent and the vascular walls. This reduces trauma to the vascular walls, when a stent is placed and removed. In the crimped state, the head ends cover the adjacent transfer segments. This significantly reduces the risk of injury to the adjacent vascular walls.

Overall, a support frame is provided with a high radial stiffness in the supporting state. This guarantees excellent and uniform bracing of the vascular wall and a functionally effective support. The configuration of the segment struts in accordance with the invention prevents excessive notch stress. The stent according to the invention can therefore be easily crimped and widened. For example, the stent can be placed on a balloon catheter and easily moved along the winding path of a body vessel. The ease of movement provides a high safety level during the implantation for both the operator and for the patient.

BRIEF DESCRIPTION OF THE DRAWING

An exemplary embodiment of the invention will now be described with reference to the drawings, in which.

DETAILED DESCRIPTION OF PREFERRED EMBODIMENTS

Figure 1:
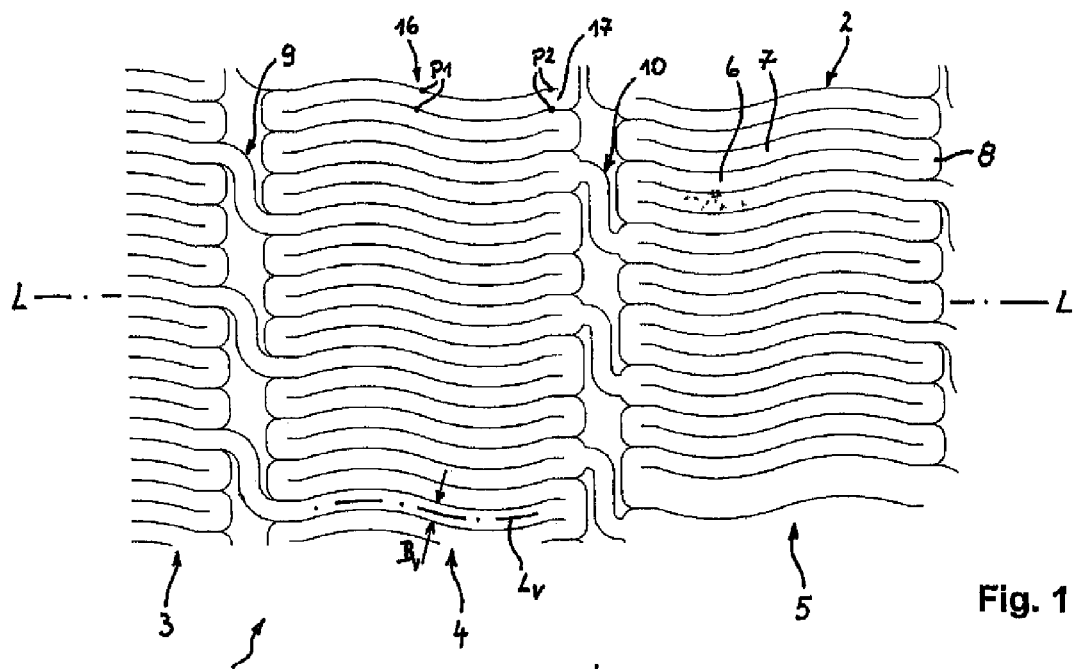
FIG. 1 shows a developed view of a section from a pattern of a stent according to the invention in an initial state.
Figure 2:
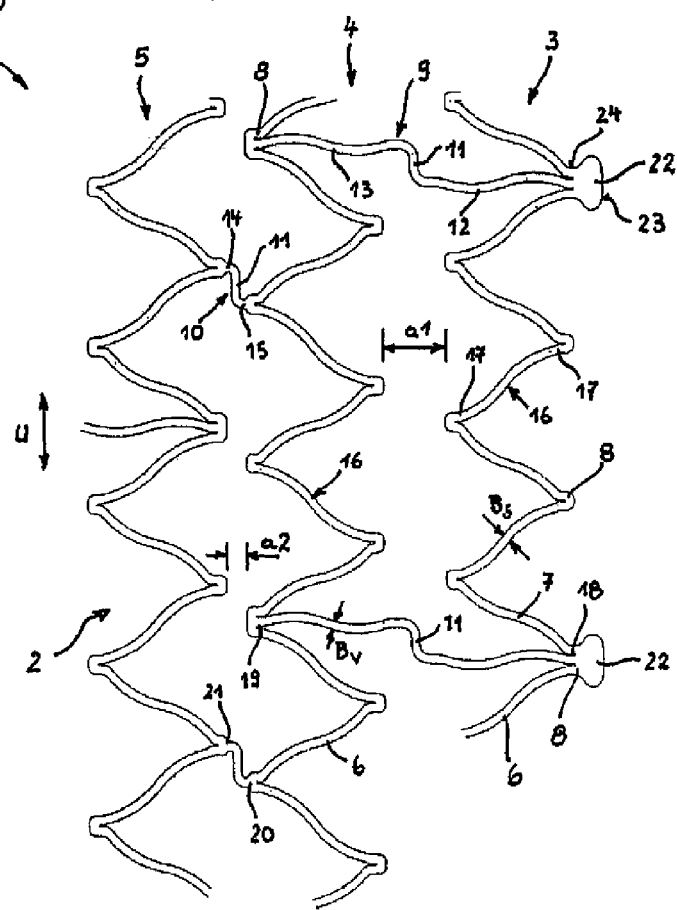
FIG. 2 shows an end section of the stent in the supporting state.

FIGS. 1 and 2 each show a developed view of a section from the layout pattern of a stent 1 according to the invention. FIG. 1 shows the layout of stent 1 in an unexpanded initial state. FIG. 2 shows the layout of the stent pattern in the expanded supporting state.

Stent 1 is made of a metal, in particular nitinol, and has a tubular support frame 2 comprised of several sequentially arranged ring segments 3, 4, 5. The stent 1 can generally have different lengths. FIGS. 1 and 2 do not show the total number of a ring segments 3, 4, 5 of the stent 1.

The ring segments 3, 4, 5 are formed by segment struts 6, 7 which are joined by tie bars 9, 10 in a sequential endless pattern. Depicted are first long tie bars 9 and second short tie bars 10. An arm 11 extending in the circumferential direction U of the support frame 2 is provided in each tie bar 9, 10. The arm 11 is connected on both sides via axial sections 12, 13; 14, 15 to a transition 8. The arms 11 are each arranged in the space between adjacent ring segments 3, 4 and 4, 5, respectively, at an axial distance a1, a2. As clearly seen in FIG. 2, the distances a1 and a2 between the ring segments 3 and 4 and the ring segments 4 and 5, respectively, in the expanded supporting state of the stent 1 have different dimensions, with a1 being greater than a2.

Figure 3:
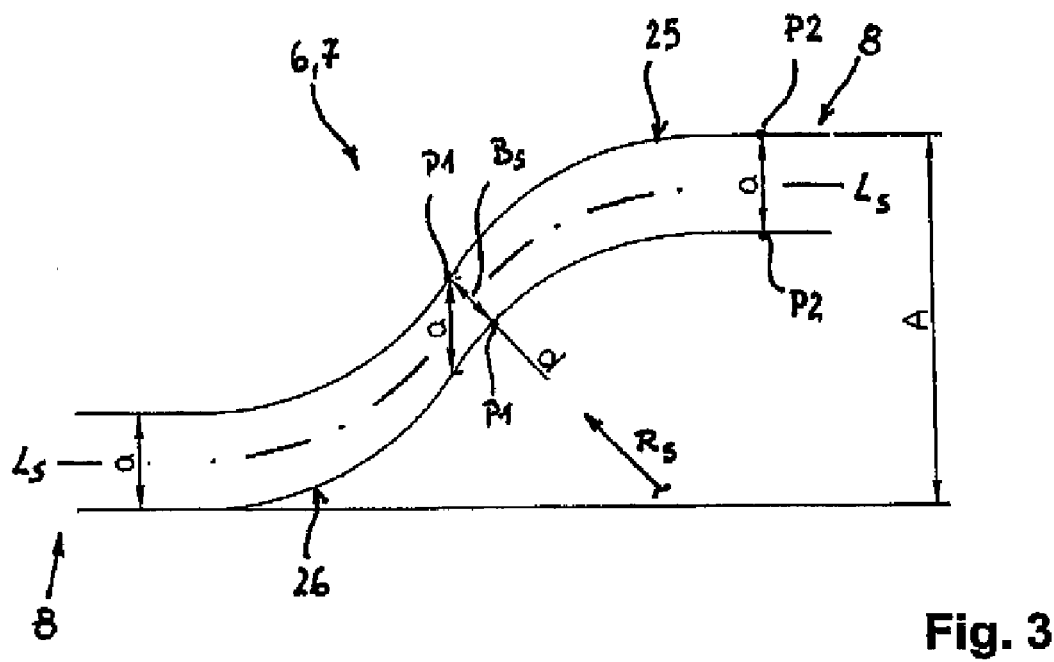
FIG. 3 shows a first model of a segment strut.
Figure 4:
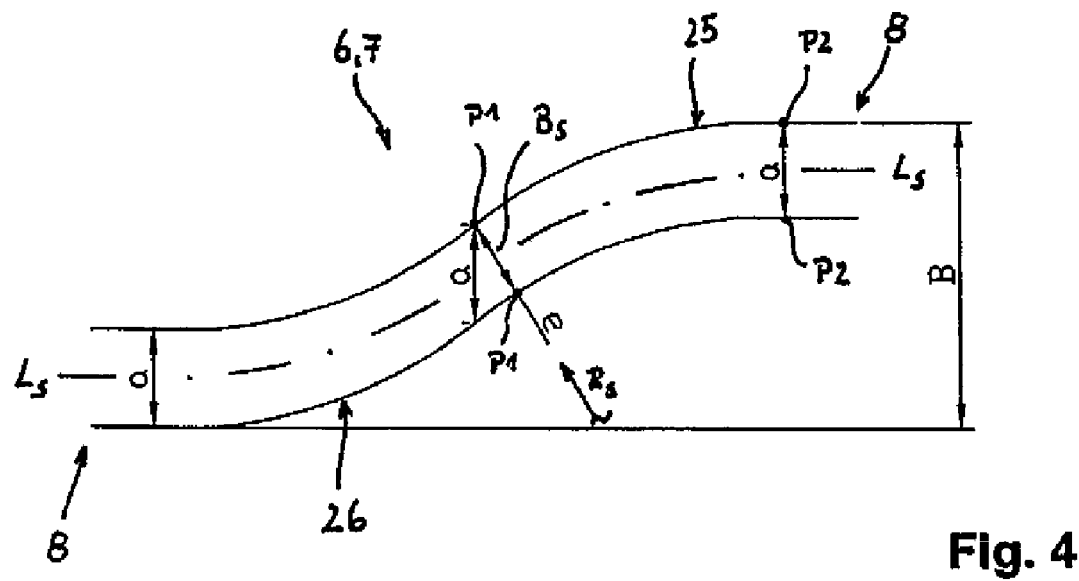
FIG. 4 shows a second model of a segment strut.

The segment struts 6, 7 are curved in a wave-like manner (see also FIGS. 3 and 4). The width $B_s$ of each segment strut 6, 7, as measured perpendicular to the longitudinal axis $L_s$ of the struts, increases from midsection 16 toward the transitions 8. The segment struts 6, 7 in midsection 16 between the points P1 are narrower than at the ends 17 between the points P2. The radius $R_s$ changes along the length of a segment strut 6, 7 and increases from midsection 16 toward the transitions 8. Internal stress generated in the segment struts 6, 7 by an exterior load in the supporting state in a body vessel is thereby distributed over the entire length of a segment strut 6, 7. Stress to the ends 17 carrying a higher load is relieved by the greater width $B_s$ at that point. This reduces the risk of fracture in the critical regions at the transition between the ends 17 of the segment struts 6, 7 and the transitions 8.

The axial sections 12, 13 of the first tie bars 9 have a wave-like curvature which conforms to the contour of the segment struts 6, 7. The width $B_v$ of the axial sections 12 and 13, as measured perpendicular to the longitudinal axis $L_v$ of the axial sections 12 and 13, increases from the arm 11 toward the transitions 8.

The axial sections 12, 13 of the first tie bars 9 extend from the bottom section 18 of two interconnected segment struts 6, 7 of a ring segment 3 to the bottom 19 of two interconnected segment struts 6, 7 of an adjacent ring segment 4. Conversely, each of the second tie bars 10 extends from the tip 20 of two interconnected segment struts 6, 7 of a ring segment 4 to the tip 21 of two interconnected segment struts 6, 7 of an adjacent ring segment 5. The first tie bars 9 and the second tie bars 10 are offset in the circumferential direction U from ring segment 3, 4 to ring segment 4, 5.

As seen in FIG. 2, the end face of each third transition 8 on the terminal ring segments 3 has a widened head end 22 which protrudes axially beyond the adjacent transitions 8. Each head end 22 has a convex round end section 23 and concave round valley sections 24 toward the transitions 8. In the crimped state, the valley sections 24 of the head ends 22 overlap and cover the adjacent transitions 8. The adjacent transitions 8 are then protected and covered by the head ends 22. This causes less trauma to the vascular walls during insertion and removal of a stent 1. The rounded head ends 22 also provide a gentle contact between the stent 1 and the vascular wall during placement.

FIGS. 3 and 4 depict two models of a segment strut 6 and 7, showing the width along the length of the segment struts 6, 7.

The width a is the same at the beginning and at the end of a segment strut 6, 7. The width a in the circumferential direction U is also equal to "a" over the entire length of the segment strut 6, 7. The width $B_s$ measured perpendicular to the longitudinal axis $L_s$ of the strut increases from midsection 16 toward the transitions 8. The increase in width depends on the incline and the wave radius $R_s$ of a segment strut 6 or 7, respectively. The transitions 25, 26 to the transitions 8 are also formed with a radius. Accordingly, a continuous transition exists from the segment width a to the segment width $B_s$ in midsection 16, as measured in the perpendicular direction. This contour produces a continuous deformation when a stent 1 is expanded.

A comparison between the models depicted in FIGS. 3 and 4 illustrates that the segment width can be readily adjusted by changing the distances A and B between the beginning of a segment and the end of a segment. If the distance A is selected to be greater than the distance B, then the perpendicular width d is necessarily smaller than the perpendicular width e (A>B→d<e).

Figure 5:
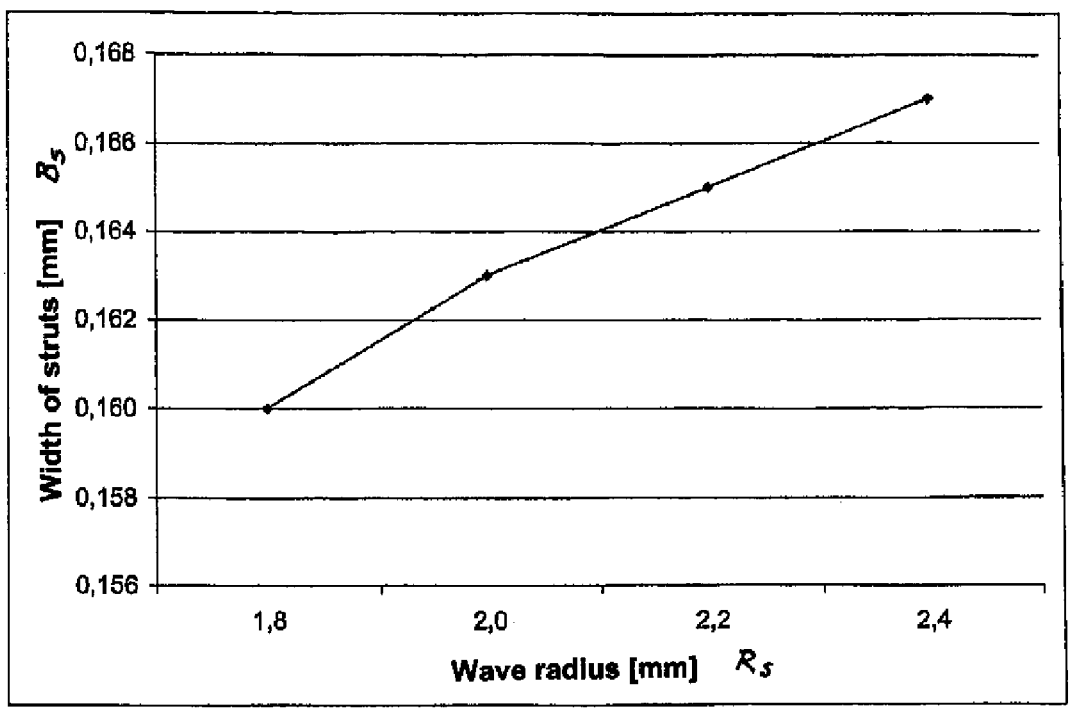
FIG. 5 shows a diagram with the width of a segment strut as a function of the wave radius.

FIG. 5 shows a diagram with the width $B_s$ of a segment strut 6, 7 as a function of the wave radius $R_s$. Only a portion of the length of a segment strut 6, 7 is shown. The width $B_s$ of the strut is 0.16 mm in midsection with a radius $R_s$ of 1.8 mm. The width $B_s$ of the strut increases approximately constantly toward the end. As seen in FIG. 5, the wave radius $R_s$ is approximately 2.4 mm at a width $B_s$ of the strut of 0.167 mm. In an actually measured exemplary embodiment, the width $B_s$ of the strut is 0.175 mm at the end of a segment strut. In general, the ratio of a wave radius $R_s$ to the width $B_s$ of the strut should be increasing in a range between approximately 10:1 and 15:1.

Figure 6:
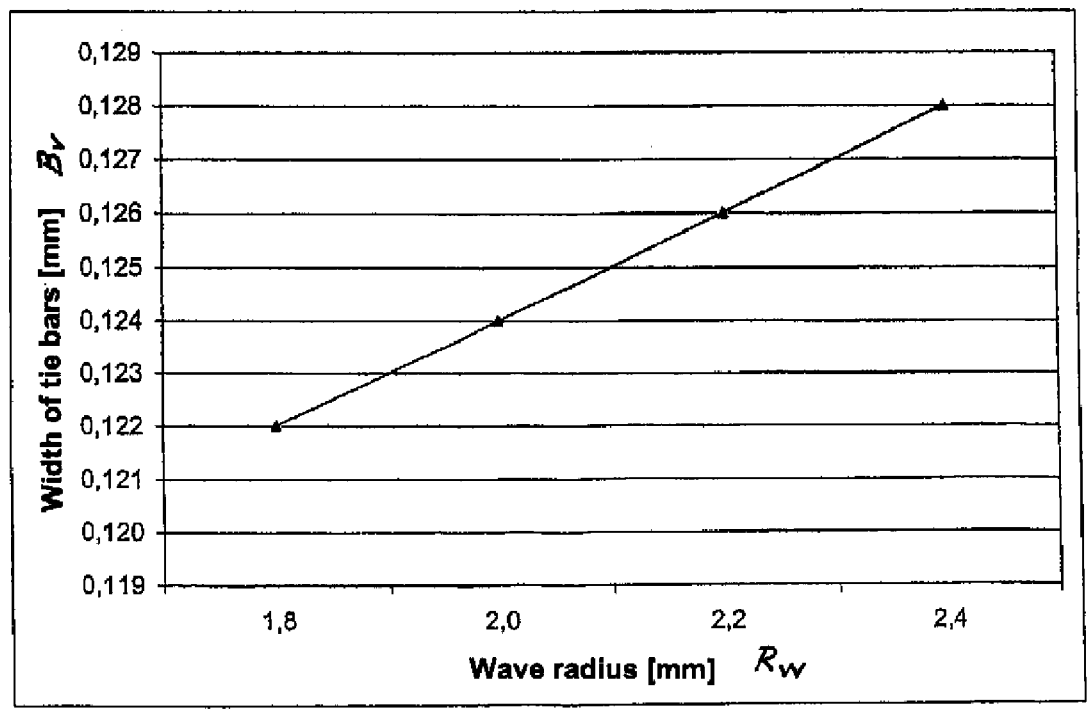
FIG. 6 shows a diagram with the width of a tie bar as a function of the wave radius.

FIG. 6 shows the width $B_v$ of a tie bar 9 and of an axial section 12, 13, respectively, as a function of the wave radius $R_w$. The ratio of a wave radius $R_w$ to width $B_v$ of the tie bars increases linearly. The ratio of the wave radius $R_w$ to width $B_v$ of a tie bar increases from the center toward the transitions 8 from 12:1 to 20:1.

The invention claimed is:

1. A stent for application in a body vessel, comprising a tubular support frame defining a longitudinal axis and expandable from an initial state to a support state, said support frame including
    plural ring segments arranged sequentially in a direction of a longitudinal axis and formed by struts having a wavy configuration and adjoining each other continuously via transitions, with each strut having a width which as measured transversely to the longitudinal axis increases from midsection in a direction to the transitions, and
    first and second tie bars for connecting neighboring ring segments, each of the tie bars including an arm extending in circumferential direction of the support frame and terminating on both ends in axial sections of wavy configuration for connection of the first and second tie bars to the transitions, with the axial sections of the first tie bars having a width which as measured transversely to the longitudinal axis increases from the arm in a direction to the transitions,
    wherein each of the first tie bars extends from a bottom of two interconnected struts of a ring segment to an opposing bottom of two interconnected struts of an adjacent ring segment, with the bottoms disposed offset to another,
    wherein each of the second tie bars extends from a tip of two interconnected struts of a ring segment to an opposing tip of two interconnected struts of an adjacent ring segment, with the tips disposed offset to one another, and
    wherein in support state of the support frame the first bars are sized to extend substantially in a direction of the longitudinal axis, and the second tie bars are sized to substantially extend in a direction transversely to the longitudinal.

2. The stent of claim 1, wherein the arms are arranged between adjacent axially spaced ring segments.

3. The stent of claim 1, wherein the first tie bars and the second tie bars are arranged between the ring segments at an offset relationship in the circumferential direction of the support frame.

4. The stent of claim 1, wherein each third of the transitions has an end formed with a widened head which protrudes in the axial direction beyond neighboring ones of the transitions.

5. The stent of claim 4, wherein the widened head is connected to a connection point formed by one of the first tie bars and two corresponding interconnected struts of a ring segment.

6. The stent of claim 1, wherein an increase in width of the strut depends on a wave radius of the strut.

7. The stent of claim 6, wherein a ratio of the wave radius to the width of the strut changes from midsection toward ends of the strut is 10:1 to 15:1.

8. The stent of claim 1, wherein a ratio of a wave radius of the axial sections to a width of the axial sections changes from the arm to the ends in a range between 12:1 and 20:1.

* * * * *